(12) United States Patent
Forsell

(10) Patent No.: US 6,210,347 B1
(45) Date of Patent: Apr. 3, 2001

(54) REMOTE CONTROL FOOD INTAKE RESTRICTION DEVICE

(76) Inventor: Peter Forsell, Gotalandsvagen 155, S-125 35, Alvsjo (SE)

( * ) Notice: Subject to any disclaimer, the term of this patent is extended or adjusted under 35 U.S.C. 154(b) by 0 days.

(21) Appl. No.: 09/133,319

(22) Filed: Aug. 13, 1998

(51) Int. Cl.$^7$ ................................................ A61B 5/103
(52) U.S. Cl. ............................ 600/593; 128/899; 600/32
(58) Field of Search .................................. 600/593, 151, 600/157, 30, 31, 32, 38, 40; 604/97, 99, 51, 28; 128/898, 899

(56) References Cited

U.S. PATENT DOCUMENTS

| | | |
|---|---|---|
| 4,592,339 | 6/1986 | Kuzmak et al. |
| 4,592,355 | 6/1986 | Antebi . |
| 4,696,288 | 9/1987 | Kuzmak et al. |
| 5,074,868 | 12/1991 | Kuzmak . |
| 5,226,429 | 7/1993 | Kuzmak . |
| 5,509,888 * | 4/1996 | Miller ............................. 128/DIG. 25 |
| 5,771,903 | 6/1998 | Jakobsson . |
| 5,938,669 | 8/1999 | Klaiber . |

FOREIGN PATENT DOCUMENTS

| | | |
|---|---|---|
| 611 561 | 8/1994 | (EP) . |
| WO 94/27504 | 12/1994 | (WO) . |

* cited by examiner

Primary Examiner—Cary O'Connor
Assistant Examiner—Pamela L Wingood
(74) Attorney, Agent, or Firm—Nixon & Vanderhye P.C.

(57) ABSTRACT

A food intake restriction device for forming a stoma opening in the stomach or esophagus of a patient, comprises an elongated restriction member to be formed into at least a substantially closed loop defining a restriction opening, and a controllable adjustment device for adjusting the restriction member in the loop to change the size of the restriction opening. The device further comprises a wireless remote control for controlling the adjustment device from outside the patient's body in a non-invasive manner to assist in treating the patient for morbid obesity.

116 Claims, 4 Drawing Sheets

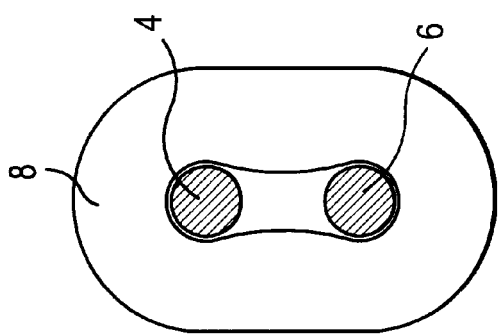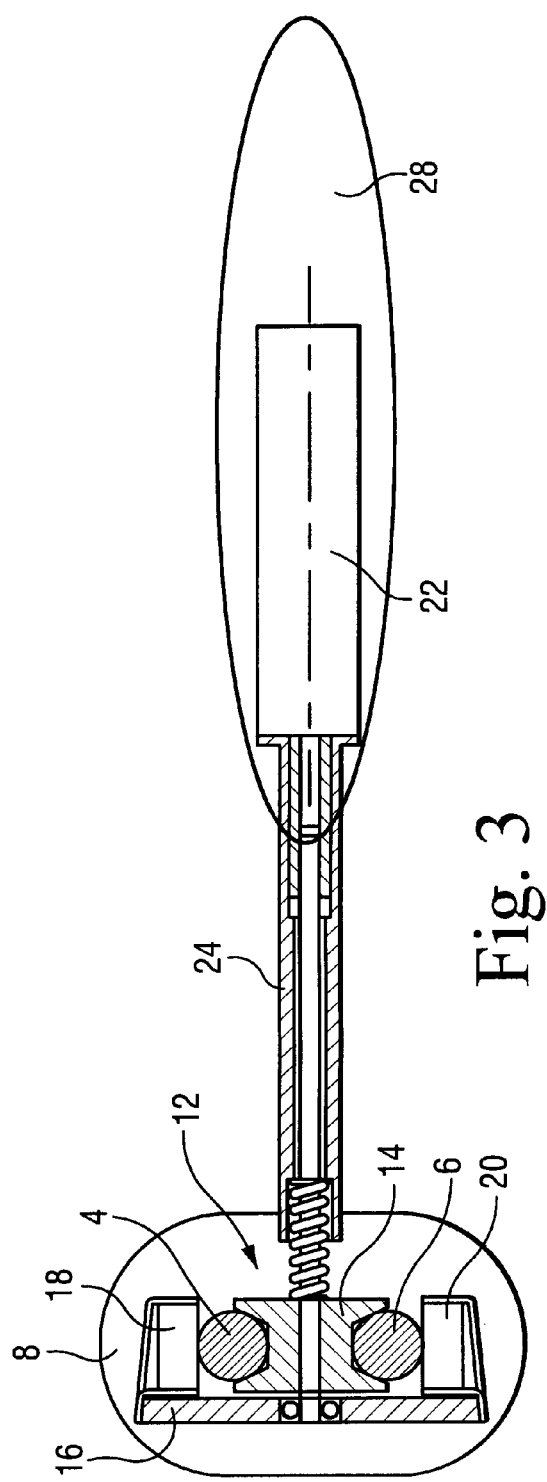

REMOTE CONTROL FOOD INTAKE RESTRICTION DEVICE

BACKGROUND AND SUMMARY OF THE INVENTION

The present invention relates to a food intake restriction device for the treatment of morbid obesity. More specifically, the invention relates to a food intake restriction device for surgical application in the abdomen of a patient for forming a stoma opening in the stomach or esophagus of the patient.

Food intake restriction devices in the form of gastric banding devices, in which a band encircles a portion of the stomach, have been used in surgery for morbid obesity to form a small gastric pouch above the band and a reduced stoma opening in the stomach. Although such a band is applied around the stomach to obtain an optimal stoma opening during surgery, some prior gastric banding devices are provided with an adjustment means enabling a minor post-operation adjustment of the size of the stoma opening. In all such prior devices, such as disclosed in U.S. Pat. No. 4,592,339, European Patent No. 0611561 and International Patent Application WO 94/27504, the adjustment means comprises an inflatable cavity in the band and an injection port in fluid connection with the inflatable cavity for adding fluid to or withdrawing fluid from the inflatable cavity. In practice, the band is made of silicone rubber which is a material approved for implantation and the fluid is a liquid such as an isotonic salt solution.

It has been found that the volume of said gastric pouch above the band increases in size up to ten times after the operation. Therefore the pouch volume during surgery needs to be very small, approximately 7 ml. To enable the patient to feed the stomach with sufficient nutrition immediately after the operation considering such a small gastric pouch, the stoma initially needs to be relatively large and later needs to be substantially reduced, as the pouch volume increases. Furthermore, the size of the stoma opening has to be gradually reduced during the first year after surgery as the gastric pouch increases in size. As indicated above, the reduction of the stoma opening using the prior art gastric banding devices is achieved by adding liquid to the cavity of the band via the injection port to expand the band radially inwardly.

A great disadvantage of repeatedly injecting liquid via the injection port is the increased risk of the patient getting an infection in the area surrounding the injection port. If such an infection would occur the injection port has to be surgically removed from the patient. Moreover, such an infection might be spread along the tube interconnecting the injection port and the band to the stomach causing even more serious complications. Thus, the stomach might be infected where it is in contact with the band, which might result in the band migrating through the wall of the stomach. Also it is uncomfortable for the patient when the necessary, often many, post-operation adjustments of the stoma opening are carried out using an injection needle penetrating the skin of the patient into the injection port.

Further, the patient may swallow pieces of food that are too large to pass the restricted stoma opening. At such an occasion the patient has to visit a doctor who can remove the food pieces, if the band design so permits, by withdrawing some liquid from the band to enlarge the stoma opening to allow the food pieces to pass the stoma. Then, the doctor has to add liquid to the band in order to restore the restricted stoma opening. These measures also require the use of an injection needle penetrating the skin of the patient, which is uncomfortable for the patient.

The invention provides an adjustable food intake restriction device which permits regular post-operation adjustments that are comfortable for the patient. The present invention provides an adjustable food intake restriction device which is easy to adjust and does not require the use of an injection needle for accomplishing post-operation adjustments of the stoma opening.

In accordance with the invention a new food intake restriction device is provided for forming a stoma opening in the stomach or esophagus of a patient, comprising: an elongated restriction member, formed into at least a substantially closed loop around the stomach or the esophagus, the loop defining a restriction opening; a controllable adjustment device which adjusts the restriction member in the loop to change the size of the restriction opening; and a wireless remote control means for controlling the adjustment device from outside the patient's body (i.e. in a non-invasive manner). Thus, the new device does not require use of an injection needle for later adjustments of said restriction opening, thereby eliminating the infection risk discussed above in connection with prior art food intake devices. [An injection port may be provided for enabling, normally a single, once-and-for-all, calibration of the amount of fluid in adjustment device if it utilizes pneumatic or hydraulic components.] Furthermore, the use of the wireless remote control of the new device for controlling the adjustment device is comfortable for the patient.

In accordance with a broad aspect of the invention, the wireless remote control means comprises separate signal transmitting means and signal receiving means, the receiving means for controlling the adjustment device in response to signals received from the signal transmitting means. The remote control means comprises a motor for operating the adjustment device and an energizer unit for providing energy. The signal receiving means comprises a control unit adapted to power the motor with energy provided by the energizer unit in response to signals received from the signal transmitting means. Any known or conventional signal transmitting or receiving device that is suitable for use with a human or mammal patient may be provided s the signal transmitting or receiving means.

The invention also relates to a method of treating morbid obesity, comprising: (a) surgically implanting in the abdomen of a patient with morbid obesity a food intake restriction device which forms a stoma opening in the stomach or esophagus, by forming an elongated restriction member (e.g. of bio-compatible material, or covered with bio-compatible material) into at least a substantially closed loop around the stomach or the esophagus of the patient, the loop defining a restriction opening; and then (b) when necessary for the patient's health or desired progress, in a non-invasive procedure, using a wireless remote control device to adjust the restriction member to change the size of the restriction opening. In the method (a) may be practiced in part by implanting an electric motor which is part of an adjustment device for acting on the restriction member to control the size of the restriction opening; and (b) may be practiced by transmitting electromagnetic wave signals from outside the patient's body to inside the patient's body, and ultimately transforming the electromagnetic wave signals into electrical energy for powering the motor.

In the method, (a) may be practiced using laparoscopic techniques, e.g. (i) inflating the patient's abdomen with gas by penetration of the patient's skin, (ii) introducing at least two laparoscopic trocars into the abdomen to introduce the elongated restriction member and one or more medical instruments, and then (iii) forming the elongated restriction member into the at least substantially closed loop. Further, (b) may be practiced by sending electromagnetic waves through the skin into the abdomen, and in the abdomen transforming the waves into an electric current which is used to adjust the restriction member.

The motor may be any type of motor, such as a pneumatic, hydraulic or electric motor, and the energizer unit may power the motor with pressurized gas or liquid, or electrical energy, depending on the type of motor. Where the motor is an electric motor, it may power pneumatic or hydraulic equipment.

In accordance with a first particular embodiment of the invention, the energizer unit comprises a power supply and the control unit powers the motor with energy from the power supply. Preferably, the power supply is an electric power supply, such as a battery, and the motor is an electric motor. In this case, the battery also continuously powers the circuitry of the signal receiving means between adjustment operations, in order to keep the signal receiving means prepared for receiving signals transmitted from the signal transmitting means.

In accordance with a second, preferred, particular embodiment of the invention, the motor is an electric motor, the signal transmitting means transmits electromagnetic wave signals and the energizer unit draws radiant energy from the electromagnetic wave signals as they are transmitted to the signal receiving means and transfers the radiant energy into electric energy for powering the electric motor. This embodiment is particularly simple and does not require any recurrent invasive measures for exchanging empty power supplies, such as batteries, that is required in the first embodiment described above. This second embodiment is only practicable if the adjustment device is of a type that requires very little power for its operation, because in practice the electromagnetic wave signals transmitted in this connection are of low power.

To expand the field of application of the second preferred embodiment to adjustment devices of the type that require more, but still relatively low, power for operation, the energizer unit advantageously comprises a rechargeable electric power supply for storing the electric energy and the control unit is adapted to power the electric motor with energy from the rechargeable electric power supply in response to signals received from the signal transmitting means. In an initial charging step the rechargeable power supply can be charged over a relatively long time (e.g. a few seconds up to a half hour) without powering the electric motor. In a following operating step, when the power supply has been charged with sufficient energy, the control unit powers the electric motor with energy from the charged power supply to operate the adjustment device, so that a desired change of the patient's stoma opening is achieved. If the capacity of the power supply is significant to achieve the necessary adjustment in one single operating step, the above steps may conveniently be repeated until the desired adjustment is achieved.

The electric power supply suitably comprises an inexpensive simple capacitor. In this case, the electric motor may be a stepping motor.

In accordance with a third particular embodiment of the invention, the energizer unit comprises a battery, an electrically operable switch for connecting the battery to the signal receiving means in an "on" mode when the switch is powered and to keep the battery disconnected from the signal receiving means in a "standby" mode when the switch is unpowered, and a rechargeable electric power supply for powering the switch. The control unit powers the electric motor with energy from the battery in response to signals received from the signal transmitting means, when the switch is in its "on" mode. Advantageously, the signal transmitting means transmits electromagnetic wave signals and the energizer unit draws radiant energy from the electromagnetic wave signals as they are transmitted to the signal receiving means and transfers the radiant energy into a current for charging the rechargeable electric power supply, which suitably is a capacitor. This energy is then used to change the switch from "off" (standby mode) to "on". This embodiment is suited for adjustment devices of the type that require relatively high power for their operation and has the advantage that the electronic circuitry of the signal receiving means does not have to be powered by the battery between adjustment operations, as is the case in the above described first embodiment of the invention. As a result, the life-time of the battery can be significantly prolonged.

In the above-described second and third embodiments of the invention in which the energizer unit draws radiant energy from electromagnetic wave signals, the energizer unit suitably comprises a coil connected to the signal receiving means for inducing an alternating current as electromagnetic wave signals are transmitted through the coil to the signal receiving means, and a rectifier for rectifying the alternating current. The rectified current is used for charging the rechargeable power source, for instance a capacitor.

Although the above-described embodiments of the invention may very well be implemented in connection with the prior types of gastric banding devices discussed above, in which the adjustment device comprises an inflatable cavity of a restriction member, it is preferred to use an elongated restriction member which is non-inflatable, in order to avoid the risk of fluid leaking from the cavity. Furthermore, it is preferred to use an adjustment device which is designed to mechanically adjust the non-inflatable restriction member, such as shown in a copending application entitled "Mechanical Food Intake Restriction Device" filed on the same date as this application (attorney docket 2333-11), the disclosure of which is hereby incorporated by reference herein.

It is the primary object of the present invention to provide an advantageous yet relatively simple assembly and method for treating morbid obesity in a substantially non-invasive manner after initial surgical implantation of a restriction member. This and other objects will become clear from the detailed description and from the appended claims.

BRIEF DESCRIPTION OF THE DRAWINGS

FIGS. 2 and 3 are cross-sectional views taken along the lines II—II and III—III, respectively, of FIG. 1;

DETAILED DESCRIPTION OF THE DRAWINGS

Figure 1:
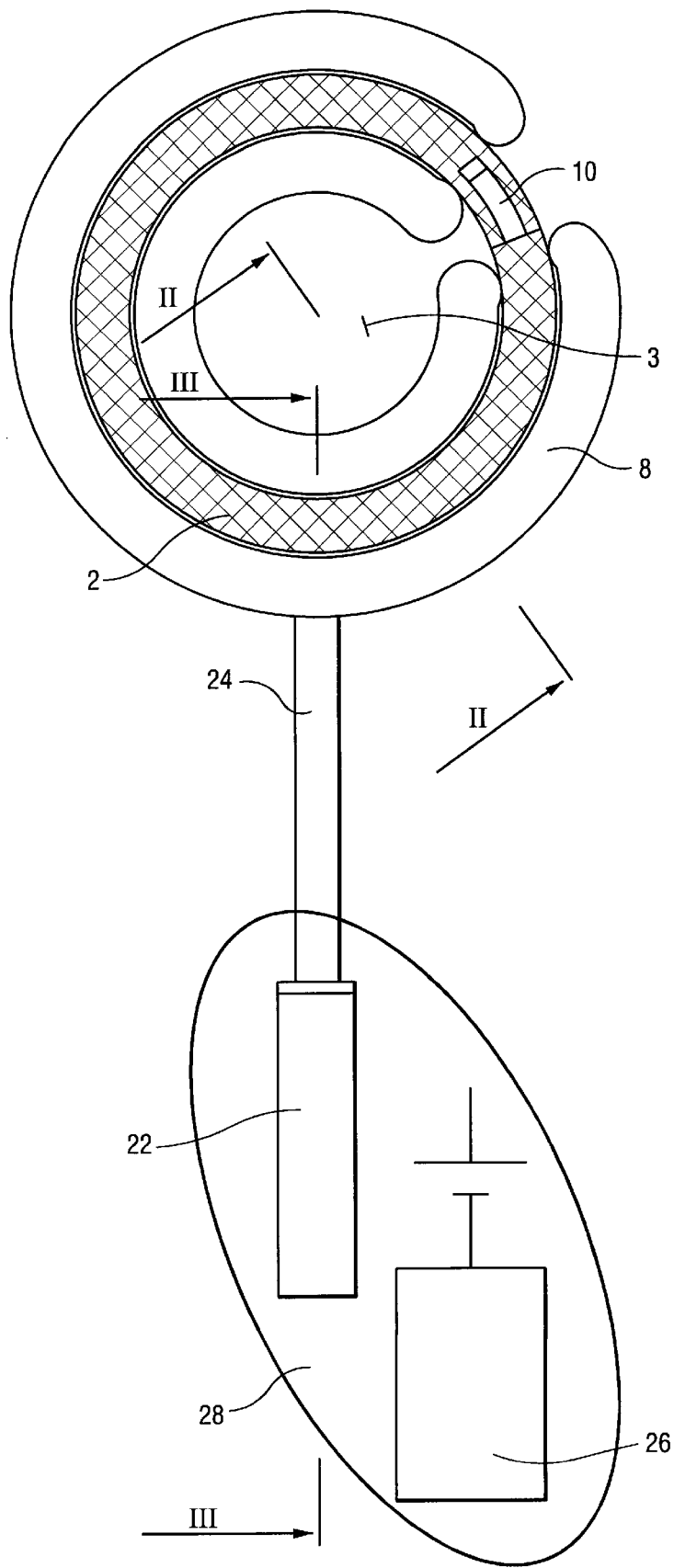
FIG. 1 is a schematic cross-sectional view of an implantable part of the adjustable food intake restriction device in accordance with the present invention.

Referring to the drawing figures, like reference numerals designate identical or corresponding elements throughout the several figures.

FIGS. 1–3 show an example of an implantable part of the device of the invention, comprising a circular resilient non-inflatable restriction member 2 with two overlapping end portions 4,6. The restriction member 2 defines a substantially circular restriction opening 3 and is enclosed in an elastic soft hose 8 except at a releasable and lockable joint 10 of the restriction member 2, which when released enables application of the restriction member 2 with its hose 8 around the esophagus or stomach of a patient in a surgical procedure. All of the in body components are desirably of bio-compatible material, or covered with bio-compatible material.

An adjustment device 12 mechanically adjusts the longitudinal extension of the restriction member 2 to change the size of said restriction opening. The adjustment device 12 may comprise any known or conventional mechanical device (e.g. inflatable gastric band) for this purpose, or those illustrated and described in the above-mentioned co-pending application. The illustrated embodiment of the device 12 comprises a pulley 14 in frictional engagement with the overlapping end portions 4,6. The pulley 14 is journalled on a holder 16 placed in the hose 8 and provided with two counter pressure rollers 18,20 pressing the respective end portions 4, 6 against the pulley 14 to increase the frictional engagement therebetween. An electric motor 22 is connected to the pulley 14 via a long flexible drive shaft 24 and is molded together with an energizer unit 26 in a body 28 of silicone rubber. The length of the flexible drive shaft 24 is selected so that the body 28 can be placed in a desired position in the abdomen of the patient. All components are of bio-compatible material, or covered with bio-compatible material.

If the patient some time after the operation needs adjustment of the restriction opening 3 of the restriction member 2, the energizer unit 26 is controlled to power the electric motor 22 either to rotate the pulley 14 in one direction to reduce the diameter of the circular restriction member 2 or to rotate the pulley 14 in the opposite direction to increase the diameter of the restriction member 2.

It should be understood that the implantable part of the device described above alternatively may be one of a variety of different adjustable designs. For example, the elongated restriction member may be inflatable by a fluid, which is pumped to and from the restriction member by a pump operated by the motor 22.

Figure 4:
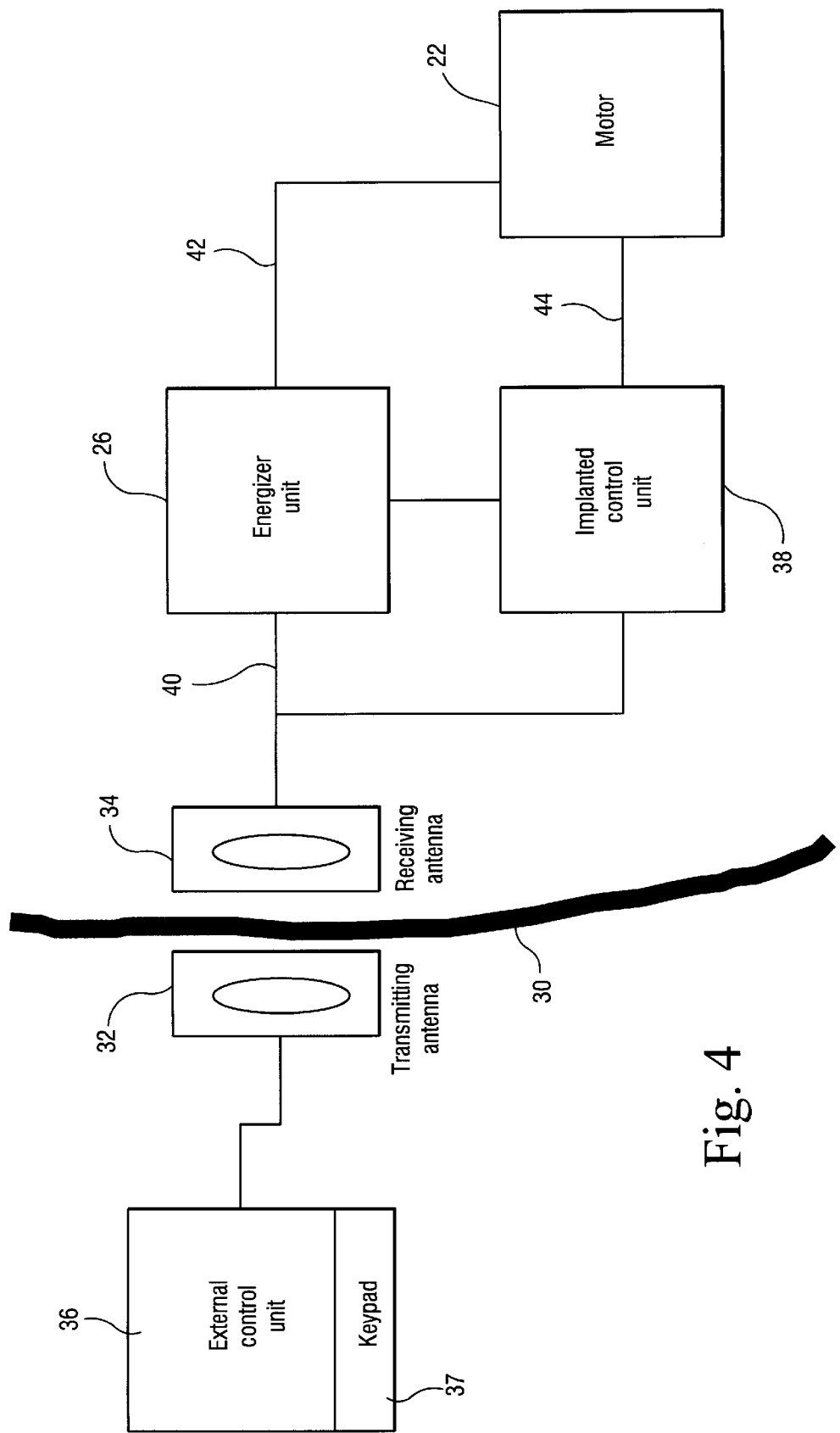
FIG. 4 is a block diagram illustrating remote control components of the device of the invention.

FIG. 4 shows the basic parts of a remote control system of the device of the invention including the electric motor 22. The described remote control system is based on the transmission of electromagnetic wave signals, often of high frequencies on the order of 100 kHz–1 gHz, through the skin 30 of the patient. For the first embodiment of the invention any known or developed remote control system may be utilized; electromagnetic wave signals don't need to be transmitted. In FIG. 4, all parts placed to the left of the skin 30 are located outside the patient's body and all parts placed to the right of the skin 30 are implanted.

An external signal transmitting antenna 32 is to be positioned close to a signal receiving antenna 34 implanted close to the skin 30. As an alternative, the receiving antenna 34 may be placed, for example, inside the abdomen of the patient. The receiving antenna 34 may comprise a coil, approximately 1–100 mm, preferably about 25 mm, in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 32 comprises a coil having about the same size as the coil of the receiving antenna 34 but wound with a thick wire that can handle the larger currents that is necessary. The coil of the transmitting antenna 32 is tuned to the same specific high frequency as the coil of the receiving antenna 34.

An external control unit 36 preferably comprises a microprocessor, a high frequency electromagnetic wave signal generator, and a power amplifier. The microprocessor of the control unit 36 switches the generator on/off and modulates signals generated by the generator to send digital information via the power amplifier and the antennas 32,34 to an implanted control unit 38. To avoid accidental random high frequency fields triggering control commands, digital signal codes are used. A conventional keypad 37 placed on the external control unit 36 is connected to the microprocessor thereof. The keypad 37 is used to order the microprocessor to send digital signals to either increase or decrease the size of the restriction opening 3 defined by the loop of the restriction member 2. The microprocessor starts a command by applying a high frequency signal to the antenna 32. After a short time, when the signal has energized the implanted parts of the control system, commands are sent to increase or decrease the size of said restriction opening of the restriction member 2 in predefined steps. The commands are preferably sent as digital packets in the form illustrated below.

| Start pattern, 8 bits | Command, 8 bits | Count, 8 bits | Checksum, 8 bits |
| --- | --- | --- | --- |

The commands are sent continuously over a relatively long time period, e.g. about 30 seconds or more. When a new increase or decrease step is desired the Count byte is increased by one to allow the implanted control unit 38 to decode and understand that another step is demanded by the external control unit 36. If any part of the digital packet is erroneous, its content is simply ignored.

Through a line 40, the implanted energizer unit 26 draws energy from the high frequency electromagnetic wave signals received by the receiving antenna 34. The energizer unit 26 stores the energy in a power supply, such as a large capacitor, powers the control unit 38, and powers the electric motor 22 via a line 42.

The control unit 38 comprises a demodulator and a microprocessor. The demodulator demodulates digital signals sent from the external control unit 36. The microprocessor of the control unit 38 receives the digital packet, decodes it and, provided that the power supply of the energizer unit 26 has sufficient energy stored, sends a signal via a signal line 44 to the motor 22 to either increase or decrease the size of the restriction opening 3 of the restriction member 2 depending on the received command code.

Alternatively, the energy stored in the power supply of the energizer unit 26 may only be used for powering a switch, and the energy for powering the motor 22 may be obtained from another implanted power source of relatively high capacity, for example a battery. In this case the switch connects the battery to the control unit 38 in an "on" mode when the switch is powered by the power supply, and keeps the battery disconnected from the control unit in a "standby" mode when said switch is unpowered.

Figure 5:
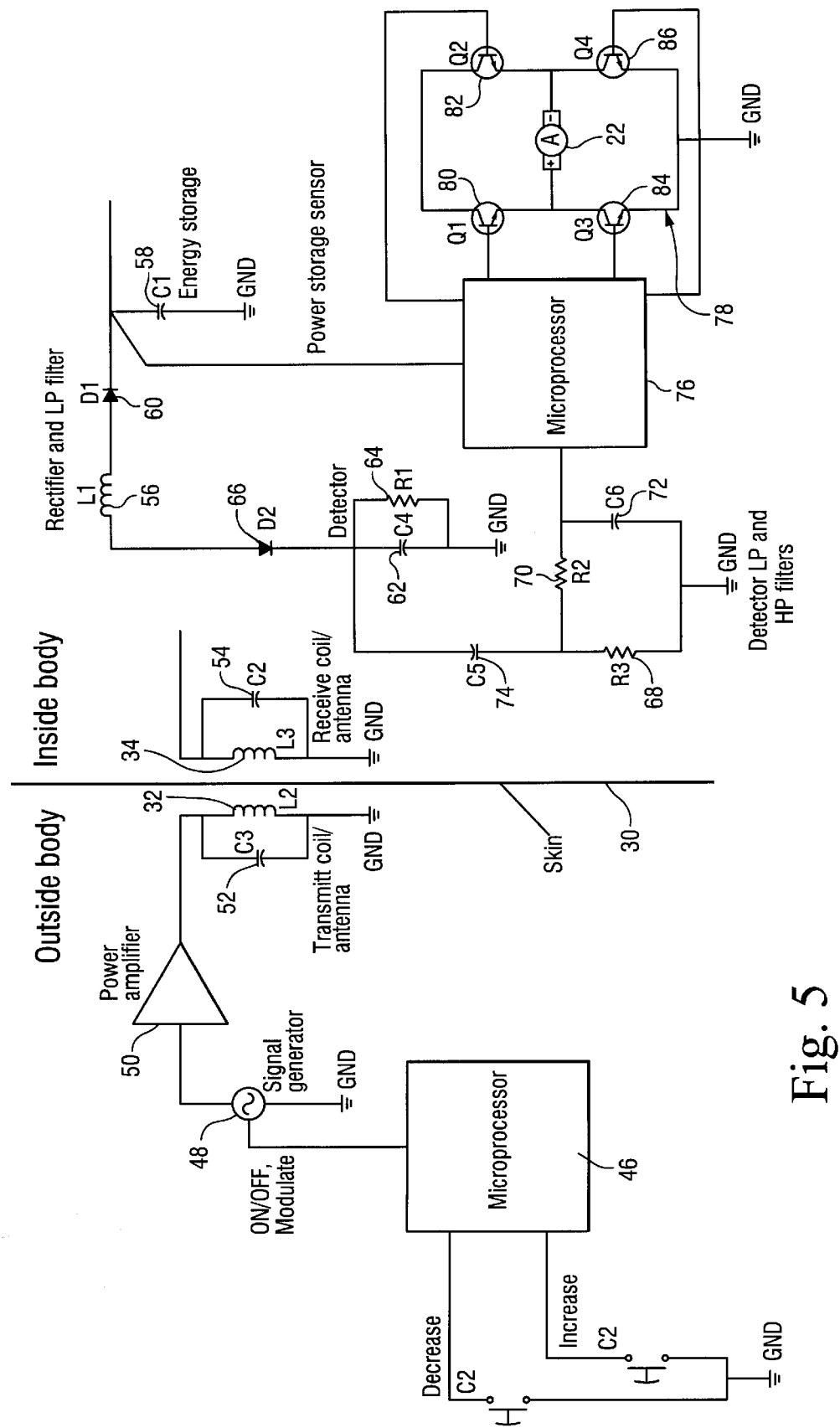
FIG. 5 is a schematic view of exemplary circuitry used for the components of the block diagram of FIG. 4.

With reference to FIG. 5, the remote control system schematically described above will now be described in accordance with a more detailed embodiment. The external control unit 36 comprises a microprocessor 46, a signal generator 48, and a power amplifier 50 connected thereto. The microprocessor 46 switches the signal generator 48 on/off and modulates signals generated by the signal generator 48 with digital commands that are sent to implanted components (to the right of skin 30 in FIG. 5) of the food intake restriction device. The power amplifier 50 amplifies the signals and sends them to the external signal transmitting antenna 32. The antenna 32 is connected in parallel with a capacitor 52 to form a resonant circuit tuned to the frequency generated by the signal generator 48.

The implanted signal receiving antenna coil 34 forms, together with a capacitor 54, a resonant circuit that is tuned to the same frequency as the transmitting antenna 32. The signal receiving antenna coil 34 induces a current from the received high frequency electromagnetic waves, and a rectifying diode 60 rectifies the induced current, which charges a storage capacitor 58. A coil 56 connected between the antenna coil 34 and the diode 60 prevents the capacitor 58 and the diode 60 from loading the circuit of the signal receiving antenna 34 at higher frequencies. Thus, the coil 56 makes it possible to charge the capacitor 58 and to transmit digital information using amplitude modulation.

A capacitor 62 and a resistor 64 connected in parallel, and a diode 66, form a detector used to detect amplitude modulated digital information. A filter circuit is formed by a resistor 68 connected in series with a resistor 70, in turn connected in series with a capacitor 72, in turn connected in series with the resistor 68 via ground, and a capacitor 74, one terminal of which is connected between the resistors 68,70 and the other terminal of which is connected between the diode 66 and the circuit formed by the capacitor 62 and resistor 64. The filter circuit is used to filter out undesired low and high frequencies. The detected and filtered signals are fed to an implanted microprocessor 76 that decodes the digital information and controls the motor 22 via an H-bridge 78 comprising transistors 80, 82, 84 and 86. The motor 22 can be driven in two opposite directions by the H-bridge 78.

The microprocessor 76 also monitors the amount of stored energy in the storage capacitor 58. Before sending signals to activate the motor 22, the microprocessor 76 checks whether the energy stored in the storage capacitor 58 is sufficient to power the motor 22. If the stored energy is not sufficient to perform the requested operation, the microprocessor 76 waits for the received signals to charge the storage capacitor 58 before activating the motor 22.

There are a number of other conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore the invention is to be accorded the broadest interpretation of the appended claims to encompass all equivalent structures, assemblies, and methods.

What is claimed is:

1. A food intake restriction device for forming a stoma opening in the stomach or esophagus of a patient, comprising:
    an elongated restriction member formed into at least a substantially closed loop around the patient's stomach or esophagus, said loop defining a restriction opening,
    a controllable adjustment device which mechanically or hydraulically adjusts said restriction member in said loop to change the size of said restriction opening,
    a wireless remote control for controlling said adjustment device from outside the patient's body; and
    wherein said remote control transfers wireless energy from outside the patient's body to implanted energy consuming components of the food intake restriction device.

2. The device according to claim 1, further comprising a motor for operating said adjustment device.

3. The device according to claim 1, further comprising an energizer unit for providing energy to implanted energy consuming components of the food intake restriction device.

4. The device according to claim 3, wherein said remote control comprises a separate signal transmitter for transmitting wireless signals from outside the patient's body.

5. The device according to claim 4, wherein said energizer unit draws energy from said wireless signals as they are transmitted by said signal transmitter.

6. The device according to claim 5, wherein said adjustment device is powered with said energy drawn from said wireless signals by said energizer unit.

7. The device according to claim 6, wherein said wireless signals comprise electromagnetic wave signals and said energizer unit draws radiant energy from said electromagnetic wave signals as they are transmitted and transfers said radiant energy into electric energy.

8. The device according to claim 3, further comprising a control unit implanted in the patient for controlling said energizer unit.

9. The device according to claim 1, wherein said remote control comprises a separate signal transmitter and a signal receiver for controlling said adjustment device in response to signals received from said signal transmitter.

10. The device according to claim 9, wherein said remote control comprises a motor for operating said adjustment device.

11. The device according to claim 10, wherein said remote control comprises an energizer unit for providing energy for the power of said motor.

12. The device according to claim 11, wherein said signal receiver comprises a control unit for powering said motor with energy provided by said energizer unit in response to signals received from said signal transmitter.

13. The device according to claim 11, wherein said energizer unit comprises a power supply.

14. The device according to claim 13, wherein said power supply is an electric power supply and said motor is an electric motor.

15. The device according to claim 14, wherein said electric power supply comprises a battery.

16. The device according to claim 12, wherein said energizer unit draws radiant energy from signals transmitted by said signal transmitter and transfers said radiant energy into electric energy.

17. The device according to claim 16, wherein said energizer unit comprises a rechargeable electric power supply for storing said electric energy.

18. The device according to claim 17, wherein said motor is an electric motor and said control unit powers said electric motor with energy from said rechargeable electric power supply in response to signals received from said signal transmitter.

19. The device according to claim 17, wherein said electric power supply comprises a capacitor.

20. The device according to claim 18, wherein said electric motor is a stepping motor.

21. The device according to claim 16, wherein said signals transmitted by said signal transmitter comprise electromagnetic wave signals.

22. The device according to claim 21, wherein said energizer unit comprises a coil connected to said signal receiver for inducing an alternating current as electromagnetic wave signals are transmitted through said coil to said signal receiver and a rectifier for rectifying said alternating current.

23. The device according to claim 12, wherein said energizer unit comprises a battery, an electrically operable switch for connecting said battery to said signal receiver in an ON mode when said switch is powered and for keeping said battery disconnected from said signal receiver in a STANDBY mode when said switch is unpowered, and a rechargeable electric power supply for powering said switch.

24. The device according to claim 23, wherein said motor is an electric motor and said control unit powers said electric motor with energy from said battery in response to signals received from said signal transmitter, when said switch is in its ON mode.

25. The device according to claim 23, wherein said energizer unit draws radiant energy from signals transmitted by said signal transmitter and transfers said radiant energy into a current for charging said rechargeable electric power supply.

26. The device according to claim 23, wherein said rechargeable electric power supply is a capacitor.

27. A food intake restriction device for forming a stoma opening in the stomach or esophagus of a patient, comprising:
an elongated restriction member formed into at least a substantially closed loop around the patient's stomach or esophagus, said loop defining a restriction opening,
a controllable adjustment device for adjusting said restriction member in said loop to change the size of said restriction opening,
a motor for operating said adjustment device, and
a wireless remote control for controlling said adjustment device from outside the patient's body.

28. The device according to claim 27, wherein said remote control transfers wireless energy from outside the patient's body to implanted energy consuming components of the food intake restriction device including said motor.

29. The device according to claim 27, further comprising an energizer unit for providing energy to implanted energy consuming components of the food intake restriction device including said motor.

30. The device according to claim 29, wherein said remote control comprises a separate signal transmitter for transmitting wireless signals from outside the patient's body.

31. The device according to claim 30, wherein said motor is powered with said energy drawn from said wireless signals by said energizer unit.

32. The device according to claim 31, wherein said motor is an electric motor, said wireless signals comprise electromagnetic wave signals and said energizer unit draws radiant energy from said electromagnetic wave signals as they are transmitted and transfers said radiant energy into electric energy.

33. The device according to claim 29, further comprising a control unit implanted in the patient for controlling said energizer unit.

34. The device according to claim 27, wherein said remote control comprises a separate signal transmitter and a signal receiver for controlling said adjustment device in response to signals received from said signal transmitter.

35. The device according to claim 34, wherein said remote control comprises an energizer unit for providing energy for the power of said motor.

36. The device according to claim 35, wherein said signal receiver comprises a control unit for powering said motor with energy provided by said energizer unit in response to signals received from said signal transmitter.

37. The device according to claim 35, wherein said energizer unit comprises a power supply.

38. The device according to claim 37, wherein said power supply is an electric power supply and said motor is an electric motor.

39. The device according to claim 38, wherein said electric power supply comprises a battery.

40. The device according to claim 36, wherein said energizer unit draws radiant energy from signals transmitted by said signal transmitter and transfers said radiant energy into electric energy.

41. The device according to claim 40, wherein said energizer unit comprises a rechargeable electric power supply for storing said electric energy.

42. The device according to claim 41, wherein said motor is an electric motor and said control unit powers said electric motor with energy from said rechargeable electric power supply in response to signals received from said signal transmitter.

43. The device according to claim 41, wherein said electric power supply comprises a capacitor.

44. The device according to claim 42, wherein said electric motor is a stepping motor.

45. The device according to claim 40, wherein said signals transmitted by said signal transmitter comprise electromagnetic wave signals.

46. The device according to claim 45, wherein said energizer unit comprises a coil connected to said signal receiver for inducing an alternating current as electromagnetic wave signals are transmitted through said coil to said signal receiver and a rectifier for rectifying said alternating current.

47. The device according to claim 36, wherein said energizer unit comprises a battery, an electrically operable switch for connecting said battery to said signal receiver in an ON mode when said switch is powered and for keeping said battery disconnected from said signal receiver in a STANDBY mode when said switch is unpowered, and a rechargeable electric power supply for powering said switch.

48. The device according to claim 47, wherein said motor is an electric motor and said control unit powers said electric motor with energy from said battery in response to signals received from said signal transmitter, when said switch is in its ON mode.

49. The device according to claim 47, wherein said energizer unit draws radiant energy from signals transmitted by said signal transmitter and transfers said radiant energy into a current for charging said rechargeable electric power supply.

50. The device according to claim 47, wherein said rechargeable electric power supply is a capacitor.

51. A food intake restriction device for forming a stoma opening in the stomach or esophagus of a patient, comprising:
an elongated inflatable restriction member formed into at least a substantially closed loop around the patient's stomach or esophagus, said loop defining a restriction opening,
a pump for pumping a fluid to and from said restriction member to inflate and deflate the restriction member to change the size of said restriction opening,
a wireless remote control for controlling said pump from outside the patient's body; and wherein said remote control transfers wireless energy from outside the patient's body to implanted energy consuming components of the food intake restriction device.

52. The device according to claim 51, further comprising a motor for operating said pump.

53. The device according to claim 51, further comprising an energizer unit for providing energy to implanted energy consuming components of the food intake restriction device.

54. The device according to claim 53, wherein said remote control comprises a separate signal transmitter for transmitting wireless signals from outside the patient's body.

55. The device according to claim 54, wherein said energizer unit draws energy from said wireless signals as they are transmitted by said signal transmitter.

56. The device according to claim 55, wherein said adjustment device is powered with said energy drawn from said wireless signals by said energizer unit.

57. The device according to claim 56, wherein said wireless signals comprise electromagnetic wave signals and said energizer unit draws radiant energy from said electromagnetic wave signals as they are transmitted and transfers said radiant energy into electric energy.

58. The device according to claim 53, further comprising a control unit implanted in the patient for controlling said energizer unit.

59. The device according to claim 57, wherein said remote control comprises a separate signal transmitter and a signal receiver for controlling said adjustment device in response to signals received from said signal transmitter.

60. The device according to claim 59, wherein said remote control comprises a motor for operating said pump.

61. The device according to claim 60, wherein said remote control comprises an energizer unit for providing energy for the power of said motor.

62. The device according to claim 61, wherein said signal receiver comprises a control unit for powering said motor with energy provided by said energizer unit in response to signals received from said signal transmitter.

63. The device according to claim 61, wherein said energizer unit comprises a power supply.

64. The device according to claim 63, wherein said power supply is an electric power supply and said motor is an electric motor.

65. The device according to claim 64, wherein said electric power supply comprises a battery.

66. The device according to claim 62, wherein said energizer unit draws radiant energy from signals transmitted by said signal transmitter and transfers said radiant energy into electric energy.

67. The device according to claim 66, wherein said energizer unit comprises a rechargeable electric power supply for storing said electric energy.

68. The device according to claim 67, wherein said motor is an electric motor and said control unit powers said electric motor with energy from said rechargeable electric power supply in response to signals received from said signal transmitter.

69. The device according to claim 67, wherein said electric power supply comprises a capacitor.

70. The device according to claim 68, wherein said electric motor is a stepping motor.

71. The device according to claim 66, wherein said signals transmitted by said signal transmitter comprise electromagnetic wave signals.

72. The device according to claim 71, wherein said energizer unit comprises a coil connected to said signal receiver for inducing an alternating current as electromagnetic wave signals are transmitted through said coil to said signal receiver and a rectifier for rectifying said alternating current.

73. The device according to claim 62, wherein said energizer unit comprises a battery, an electrically operable switch for connecting said battery to said signal receiver in an ON mode when said switch is powered and for keeping said battery disconnected from said signal receiver in a STANDBY mode when said switch is unpowered, and a rechargeable electric power supply for powering said switch.

74. The device according to claim 73, wherein said motor is an electric motor and said control unit powers said electric motor with energy from said battery in response to signals received from said signal transmitter, when said switch is in its ON mode.

75. The device according to claim 73, wherein said energizer unit draws radiant energy from signals transmitted by said signal transmitter and transfers said radiant energy into a current for charging said rechargeable electric power supply.

76. The device according to claim 73, wherein said rechargeable electric power supply is a capacitor.

77. A food intake restriction device for forming a stoma opening in the stomach or esophagus of a patient, comprising:
a non-inflatable elongated restriction member formed into at least a substantially closed loop around the patient's stomach or esophagus, said loop defining a restriction opening,
a controllable adjustment device for adjusting said restriction member in said loop to change the size of said restriction opening, and
a wireless remote control for controlling said adjustment device from outside the patient's body.

78. The device according to claim 77, wherein said remote control transfers wireless energy from outside the patient's body to implanted energy consuming components of the food intake restriction device.

79. The device according to claim 77, further comprising a motor for operating said adjustment device.

80. The device according to claim 77, further comprising an energizer unit for providing energy to implanted energy consuming components of the food intake restriction device.

81. The device according to claim 80, wherein said remote control comprises a separate signal transmitter for transmitting wireless signals from outside the patient's body.

82. The device according to claim 81, wherein said energizer unit draws energy from said wireless signals as they are transmitted by said signal transmitter.

83. The device according to claim 82, wherein said adjustment device is powered with said energy drawn from said wireless signals by said energizer unit.

84. The device according to claim 83, wherein said wireless signals comprise electromagnetic wave signals and said energizer unit draws radiant energy from said electromagnetic wave signals as they are transmitted and transfers said radiant energy into electric energy.

85. The device according to claim 80, further comprising a control unit implanted in the patient for controlling said energizer unit.

86. The device according to claim 77, wherein said remote control comprises a separate signal transmitter and a signal receiver for controlling said adjustment device in response to signals received from said signal transmitter.

87. The device according to claim 86, wherein said remote control comprises a motor for operating said adjustment device.

88. The device according to claim 87, wherein said remote control comprises an energizer unit for providing energy for the power of said motor.

89. The device according to claim 88, wherein said signal receiver comprises a control unit for powering said motor with energy provided by said energizer unit in response to signals received from said signal transmitter.

90. The device according to claim 88, wherein said energizer unit comprises a power supply.

91. The device according to claim 90, wherein said power supply is an electric power supply and said motor is an electric motor.

92. The device according to claim 91, wherein said electric power supply comprises a battery.

93. The device according to claim 89, wherein said energizer unit draws radiant energy from signals transmitted by said signal transmitter and transfers said radiant energy into electric energy.

94. The device according to claim 93, wherein said energizer unit comprises a rechargeable electric power supply for storing said electric energy.

95. The device according to claim 94, wherein said motor is an electric motor and said control unit powers said electric motor with energy from said rechargeable electric power supply in response to signals received from said signal transmitter.

96. The device according to claim 94, wherein said electric power supply comprises a capacitor.

97. The device according to claim 95, wherein said electric motor is a stepping motor.

98. The device according to claim 93, wherein said signals transmitted by said signal transmitter comprise electromagnetic wave signals.

99. The device according to claim 98, wherein said energizer unit comprises a coil connected to said signal receiver for inducing an alternating current as electromagnetic wave signals are transmitted through said coil to said signal receiver and a rectifier for rectifying said alternating current.

100. The device according to claim 89, wherein said energizer unit comprises a battery, an electrically operable switch for connecting said battery to said signal receiver in an ON mode when said switch is powered and for keeping said battery disconnected from said signal receiver in a STANDBY mode when said switch is unpowered, and a rechargeable electric power supply for powering said switch.

101. The device according to claim 100, wherein said motor is an electric motor and said control unit powers said electric motor with energy from said battery in response to signals received from said signal transmitter, when said switch is in its ON mode.

102. The device according to claim 100, wherein said energizer unit draws radiant energy from signals transmitted by said signal transmitter and transfers said radiant energy into a current for charging said rechargeable electric power supply.

103. The device according to claim 100, wherein said rechargeable electric power supply is a capacitor.

104. The device according to claim 77, wherein said adjustment device is designed to mechanically adjust said non-inflatable restriction member.

105. A food intake restriction device for forming a stoma opening in the stomach or esophagus of a patient, comprising:

an elongated restriction member formed into at least a substantially closed loop around the patient's stomach or esophagus, said loop defining a restriction opening, a controllable adjustment device which adjusts said restriction member in said loop to change the size of said restriction opening, and a wireless remote control for controlling said adjustment means from outside the patient's body, said remote control including a motor for operating said adjustment device, an energizer unit for providing energy, and a separate signal transmitter and signal receiver, said signal receiver including a control unit for powering said motor with energy provided by said energizer unit in response to signals received from said signal transmitter.

106. A method of treating morbid obesity, comprising:
(a) inflating the abdomen of a patient with morbid obesity by penetration of the patient's skin;
(b) introducing at least two laparascopic trocars into the abdomen;
(c) introducing an elongated restriction member of a food intake restriction device through the laparascopic trocars;
(d) forming the elongated restriction member into an at least substantially closed loop around the stomach or esophagus of the patient to form a stoma opening in the stomach or esophagus, the loop defining a restriction opening; and then
(e) when necessary for the patient's health or desired progress, in a non-invasive procedure, using a wireless remote control device to adjust the restriction member to change the size of the restriction opening.

107. A method as recited in claim 106, wherein (c) is practiced in part by also implanting a motor or pump which is part of an adjustment device for acting on the restriction member to control the size of the restriction opening.

108. A method as recited in claim 106, wherein (c) is practiced in part by implanting an adjustment device for acting on the restriction member to control the size of the restriction opening, and (e) is practiced by using the wireless remote control device to transfer wireless energy from outside the patient's body to the implanted adjustment device for activating the adjustment device to adjust the restriction member to change the size of the restriction opening.

109. A method as recited in claim 108, wherein (e) is practiced by using the wireless remote control device to transmit electromagnetic wave signals from outside the patient's body to inside the patient's body, and ultimately transforming the electromagnetic wave signals into energy for activating the adjustment device.

110. A method of treating morbid obesity, comprising:
(a) surgically implanting in the abdomen of a patient with morbid obesity a food intake restriction device which forms a stoma opening in the stomach or esophagus, by forming an elongated restriction member into at least a substantially closed loop around the stomach or esophagus of the patient, the loop defining a restriction opening, and an adjustment device for acting on the restriction member to control the size of the restriction member; and then
(b) when necessary for the patient's health or desired progress, in a non-invasive procedure, using a wireless remote control device to transfer wireless energy from outside the patient's body to the implanted adjustment device for activating the adjustment device to adjust the restriction member to change the size of the restriction opening.

111. A method as recited in claim 116, wherein (b) is practiced by transmitting wave signals from outside the patient's body to inside the patient's body, and ultimately transforming the wave signals into energy for activating the adjustment device.

112. A method as recited in claim 116, wherein (a) is practiced in part by implanting an electric motor or pump which is part of the adjustment device.

113. A method of treating morbid obesity, comprising:
(a) surgically implanting in the abdomen of a patient with morbid obesity a food intake restriction device which forms a stoma opening in the stomach or esophagus, by forming an elongated restriction member into at least a substantially closed loop around the stomach or esophagus of the patient, the loop defining a restriction opening, and surgically implanting a motor operatively connected to the restriction member to adjust the size of the restriction member; and then
(b) when necessary for the patient's health or desired progress, in a non-invasive procedure, using a wireless remote control device to control the motor to adjust the restriction member to change the size of the restriction opening.

114. A food intake restriction device for forming a stoma opening in the stomach or esophagus of a patient, comprising:
an elongated restriction member formed into at least a substantially closed loop around the patient's stomach or esophagus, said loop defining a restriction opening,
a controllable adjustment device which adjusts said restriction member in said loop to change the size of said restriction opening,
a wireless remote control for controlling said adjustment device from outside the patient's body, and
an implanted capacitor for storing electric energy, said wireless remote control controlling said capacitor to supply energy to implanted energy consuming components of the apparatus.

115. A food intake restriction device for forming a stoma opening in the stomach or esophagus of a patient, comprising:
an elongated restriction member formed into at least a substantially closed loop around the patient's stomach or esophagus, said loop defining a restriction opening,
a controllable adjustment device which adjusts said restriction member in said loop to change the size of said restriction opening,
a wireless remote control for controlling said adjustment device from outside the patient's body,
an implanted power supply for supplying energy to implanted energy consuming components of said device, and
a switch controlled by said wireless remote control to connect amid power supply to and disconnect said power supply from said energy consuming components.

116. A food intake restriction device for forming a stoma opening in the stomach or esophagus of a patient, comprising:
an elongated restriction member formed into at least a substantially closed loop around the patient's stomach or esophagus, said loop defining a restriction opening,
a controllable adjustment device for adjusting said restriction member in said loop to change the size of said restriction opening,
implanted energy consuming components of said device,
a wireless remote control for controlling said adjustment device from outside the patient's body, and
an implanted rechargeable power supply controlled by said wireless remote control to supply energy to said implant energy consuming components, and rechargeable from exteriorly of the patient's body.

* * * * *